United States Patent
Reeves et al.

(10) Patent No.: US 6,599,575 B2
(45) Date of Patent: Jul. 29, 2003

(54) METHOD FOR THE PRODUCTION OF A DURABLY HYDROPHILIC, NON-LEACHING COATING FOR HYDROPHOBIC SUBSTANCES

(75) Inventors: William G. Reeves, Appleton, WI (US); Li-fu Chen, West Lafayette, IN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/038,750

(22) Filed: Dec. 31, 2001

(65) Prior Publication Data

US 2003/0124257 A1 Jul. 3, 2003

(51) Int. Cl.$^7$ .................................................. B05D 3/10
(52) U.S. Cl. ........................ 427/336; 427/337; 427/339; 427/8
(58) Field of Search ................................ 427/336, 337, 427/343, 8, 339

(56) References Cited

U.S. PATENT DOCUMENTS

| 2,217,823 A | * | 10/1940 | Thor | ......................... | 106/16.2 |
|---|---|---|---|---|---|
| 3,676,382 A | * | 7/1972 | Turbak et al. | ............... | 524/752 |
| 3,852,224 A | * | 12/1974 | Bridgeford | .................... | 264/49 |
| 4,999,149 A | * | 3/1991 | Chen | ......................... | 264/187 |
| 6,051,335 A | * | 4/2000 | Dinh-Sybeldon et al. | ... | 429/142 |

* cited by examiner

*Primary Examiner*—Michael Barr
(74) *Attorney, Agent, or Firm*—Kilpatrick Stockton LLP

(57) ABSTRACT

The present invention is directed to a method for the production of a durably hydrophilic, non-leaching coating. A carbohydrate-salt mixture is formed by at least partially dissolving a water insoluble carbohydrate in an aqueous salt solution to form a carbohydrate-salt complex. The carbohydrate-salt mixture is applied to a substrate, and the substrate is rinsed with a solvent to form a coating.

44 Claims, No Drawings

METHOD FOR THE PRODUCTION OF A DURABLY HYDROPHILIC, NON-LEACHING COATING FOR HYDROPHOBIC SUBSTANCES

FIELD OF THE INVENTION

The present invention relates to a method for the production of a durably hydrophilic, non-leaching coating and the product of such a process.

BACKGROUND OF THE INVENTION

The use of carbohydrates to form coatings is well known in the art. For example, carbohydrates such as hydroxyethylcellulose can be derivatized wherein the derivative is dissolved in water and used as a coating. However, a coating formed from this type of carbohydrate derivative is water soluble and has to be further reacted to form a water insoluble coating.

Alternatively, a water insoluble cellulose derivative may be used to form a water insoluble coating. For example, cellulose acetate may be dissolved in a suitable solvent, such as acetone, to produce a coating. Unfortunately, there are no known derivatives which can be dissolved in an organic solvent to form a hydrophilic coating without further treatment of the material after coating.

In other cases, to avoid the difficulties inherent in working with flammable solvents, the cellulose derivative may be formed into an aqueous emulsion and the emulsion used to form a coating. This approach is taught in U.S. Pat. No. 3,565,669. Another means of forming a cellulosic coating is to use a water or organic solvent soluble cellulose derivative and then insolubilize the coating as taught in AU 8,317,253 and JP 5,210,893.

What is needed in the art is a method of forming a water insoluble carbohydrate coating using a one step process in which the carbohydrate may be dissolved directly in a water-based solution, without the formation of a derivative. Such a process would offer significant economic and environmental advantages over the prior art. Direct dissolution of the carbohydrate avoids the additional cost of derivatizing a polysaccharide and further chemically modifying the derivative.

SUMMARY OF THE INVENTION

The present invention solves one or more of the above described problems by providing a method for the production of a carbohydrate coating on a substrate. The method includes forming a carbohydrate-salt mixture by at least partially dissolving a water insoluble carbohydrate in an aqueous salt solution to form a carbohydrate-salt complex. The carbohydrate-salt mixture is applied to a substrate, and the substrate is rinsed with a solvent to form a coating. The coating is desirably hydrophilic and non-leaching.

More particularly, the aqueous salt solution contains a salt having a Hammett acidity between approximately +2 and −3, such as zinc chloride. The carbohydrate is desirably cellulose, starch, pectin, alginic acid, chitin or chemical derivatives thereof. In addition, the substrate may be a non-woven or woven material. Desirably, the substrate is hydrophobic.

The method of the present invention may further include adding a solvent to the carbohydrate-salt mixture to control the orientation and degree of aggregation of the carbohydrate-salt complex. Further, the method may include adding a surfactant to the carbohydrate-salt mixture to improve the application of the mixture to the substrate. The surfactant may be a cationic surfactant, an anionic surfactant or a nonionic surfactant.

Still more particularly, the method of the present invention includes heating the carbohydrate-salt mixture to a temperature between approximately 15° C. and 85° C. to allow optimal dissolution of the carbohydrate in the aqueous salt solution.

The present invention is also directed to a coated substrate made according to the method of the present invention and absorbent structures comprising the coated substrate. For example, the coated substrate of the present invention is particularly useful in personal care products such as diapers, feminine pads, panty liners, incontinence products, and training pants.

Other objects, features and advantages of this invention will become apparent upon reading the following detailed description in conjunction with the claims.

DESCRIPTION OF THE PREFERRED EMBODIMENTS

The method of the present invention provides a process of making a durably hydrophilic, non-leaching coating. The process includes at least partially dissolving a water insoluble carbohydrate in an aqueous salt solution of low Hammett acidity to form a carbohydrate-salt complex. The complex in solution may be adjusted for optimum properties as a coating for a particular substrate through control of the concentration of the salt and the molecular weight and concentration of the water insoluble carbohydrate. If necessary, the surface tension of the mixture is also adjusted to better wet the substrate. The substrate is treated with the carbohydrate-salt mixture and then washed in a solvent to remove excess salt and regenerate the water insoluble carbohydrate as a hydrophilic, non-leaching coating.

In contrast to the prior art, the method of the present invention provides for at least partial dissolution of the carbohydrate directly in a water-based solution without the use of a solvent, and without the need for the formation of a derivative which must be insolubilized in a subsequent step.

Carbohydrates, as defined in this invention, are polymers containing linked sugars. Despite being composed of sugars, which are water-soluble as individual molecules, the larger carbohydrates are water insoluble due to extensive internal hydrogen bonding between the alcohol substituents of the sugar monomers. These molecules have hydrophilic and hydrophobic regions, usually based on the degree of sidedness for the hydroxyl substituents of the sugar ring. Any carbohydrate that is water insoluble due to internal hydrogen bonding may be used in the method of the present invention. Carbohydrates suitable for use in the, present invention include, but are not limited to cellulose, starch, pectin, alginic acid, chitin or chemical derivatives thereof. Desirably, the carbohydrate is cellulose.

Depending upon the carbohydrate used, the carbohydrate-salt mixture may contain from about 0.1% to about 50% by weight carbohydrate. Desirably, the carbohydrate-salt mixture contains from about 0.1% to about 10% by weight carbohydrate.

In the present invention, metallic salts of sufficiently low Hammett acidity, such as zinc and calcium ions, are used to disrupt the internal hydrogen bonding of the carbohydrates. The metallic salts form water soluble metal complexes with the water insoluble carbohydrates and alter the arrangement of the hydrophobic and hydrophilic regions of these carbohydrates once in solution. The aqueous salt solution typically contains at least 30% by weight salt, and desirably contains from about 60% to about 80% by weight salt. Examples of salts useful in the present invention include, but are not limited to, zinc thiocyanate, zinc halides such as zinc chloride, zinc bromide and zinc iodide, cadmium thiocyanate, cadmium halides such as cadmium chloride, cadmium bromide and cadmium iodide, titanium thiocyanate, titanium halides such as titanium chloride, titanium bromide and titanium iodide, zirconium thiocyanate, zirconium halides such as zirconium chloride, zirconium bromide and zirconium iodide, lithium thiocyanate, and lithium halides, such as lithium chloride, lithium bromide and lithium iodide, calcium thiocyanate, calcium halides, including calcium chloride, calcium bromide, and calcium iodide, magnesium thiocyanate, magnesium halides, including magnesium chloride, magnesium bromide, and magnesium iodide, strontium thiocyanate, strontium halides, including strontium chloride, strontium bromide, and strontium iodide, potassium thiocyanate, potassium halides such as potassium chloride, potassium bromide and potassium iodide, guanadinium thiocyanate, N-methyl morpholine oxide, or mixtures thereof. Desirably, the salt is zinc chloride because of its low cost and safety for human contact.

Hammett acidity is a measurement which is used for acidic solvents of high dielectric constant. The dielectric constant is a measure of the ion-solvating ability of the solvent. The Hammett acidity, $H_0$ is defined as:

$$H_0 = pK_{AH_W^+} + \log\frac{[A]}{[AH^+]}$$

Where [A] is the concentration of the conjugate base of the solvent acid-base pair and [AH$^+$] is the concentration of the corresponding conjugate acid. In the method of the present invention, it is desirable for the salt to have a Hammett acidity from approximately +2 to approximately −3. More desirably, the salt has a Hammett acidity from approximately 0 to approximately −2. More specifically, when dissolving cellulose from wood pulp, the Hammett acidity is desirably from about −1 to about −3. For more easily dissolved carbohydrates such as starch or very low molecular weight cellulose, the Hammett acidity is desirably from about +1 to about 0.

Examples of salts that have sufficiently low Hammett acidity to at least partially dissolve carbohydrates as insoluble as cellulose include, but are not limited to, zinc thiocyanate, zinc halides such as zinc chloride, zinc bromide and zinc iodide, cadmium thiocyanate, cadmium halides such as cadmium chloride, cadmium bromide and cadmium iodide, titanium thiocyanate, titanium halides such as titanium chloride, titanium bromide and titanium iodide, zirconium thiocyanate, zirconium halides such as zirconium chloride, zirconium bromide and zirconium iodide, lithium thiocyanate, and lithium halides, such as lithium chloride, lithium bromide and lithium iodide, or mixtures thereof. Examples of salts that have a sufficiently low Hammett acidity to dissolve relatively less insoluble carbohydrates, such as starch, include but are not limited to, calcium thiocyanate, calcium halides, including calcium chloride, calcium bromide, and calcium iodide, magnesium thiocyanate, magnesium halides, including magnesium chloride, magnesium bromide, and magnesium iodide, strontium thiocyanate, strontium halides, including strontium chloride, strontium bromide, and strontium iodide, potassium thiocyanate, potassium halides such as potassium chloride, potassium bromide and potassium iodide, guanadinium thiocyanate, N-methyl morpholine oxide, or mixtures thereof.

When mixed with an aqueous solution of one of the above salts, at least partial dissolution of the water insoluble carbohydrate will occur due to the disruption of the internal hydrogen bonds of the carbohydrate. This disruption of the internal hydrogen bonds allows formation of a carbohydrate salt complex, but some physical entanglement of the carbohydrate remains intact. Additional stirring of the mixture will break these entanglements but will lower the viscosity of the mixture. As used herein, "at least partial dissolution" means that between approximately 30% and approximately 100% of the carbohydrate dissolves in the aqueous salt solution, however the degree of dissolution depends on many factors, including the extent of physical stirring of the mixture, the temperature of the mixture, the type of salt used, the concentration of the aqueous salt solution, the type and amount of water insoluble carbohydrate used. Thus, it will be understood by those of skill in the art that variations in the above percentages of dissolution due to the above factors are within the scope of the invention. Additionally, it will be understood by those of skill in the art that degree of dissolution of the carbohydrate does not include the presence of insoluble impurities in the carbohydrate, such as lignin in the case of cellulose.

By adjusting the concentrations of the metallic ions and carbohydrate in the mixture, it is possible to control the balance of surface hydrophobicity and hydrophilicity on a substrate that has been treated with the dissolved carbohydrate, which is subsequently regenerated to its water insoluble form.

The dissolution of carbohydrate in the salt solution can take place over a range of temperatures from room temperature (about 15° C.) to about 85° C. Higher temperatures decrease the degree of polymerization (DP) of the carbohydrate. The preferred temperature for dissolution will depend upon the balance of hydrophilic/hydrophobic properties desired in the product treated with the carbohydrate mixture.

Once the carbohydrate-salt mixture is formed, it can be diluted with a solvent to control the orientation and degree of aggregation of the metal-carbohydrate complex. A suitable solvent is water. The degree of dilution is desirably down to a concentration of salt which is barely able to keep the dissolved carbohydrate in solution. During this dilution step, the carbohydrate begins to aggregate. The structure of these aggregates determines the properties of the regenerated carbohydrate coating, and may be controlled with temperature and through the addition of other substances, including additional salts, surfactants, or organic solvents.

For some substrates, the carbohydrate-salt mixture has a sufficiently low contact angle that it readily wets the substrate. However, substrates that are not readily wetted by the carbohydrate-salt mixture can be wetted if an appropriate surfactant is added to the carbohydrate-salt mixture. While there is a wide choice of surfactants to lower the surface tension of the carbohydrate-salt mixture, a surfactant can also interact with the carbohydrate to change its hydrophilic/hydrophobic balance and its orientation in solution. So far, no means have been found to predict the hydrophilicity of carbohydrate regenerated on a substrate in the presence of a surfactant, although surfactants have been identified which give desirable product performance. Surfactants that have been found to be useful include cationic surfactants, such as cetyl trimethyl ammonium bromide, anionic surfactants, such as sodium lauryl sulfonate, and nonionic surfactants, such as ethoxylated hexanol.

The carbohydrate-salt mixture can be applied to a substrate by any method known to those skilled in the art, such as dipping, spraying and foam-coating. Desirably the substrate is hydrophobic. Examples of substrates which may be coated by the method of the present invention include but are not limited to, woven or non-woven materials prepared from naturally hydrophobic polymers such as polypropylene, polyethylene, polyester, or polyamide. Mixtures of hydrophilic and hydrophobic polymers may also be coated using the method of the present invention in order to prepare a material with a uniform hydrophilicity. Furthermore, in many embodiments, particularly for use in personal care products, a preferred substrate is non-woven material. As used herein, the term "non-woven material" refers to material that has a structure of individual fibers or filaments randomly arranged in a mat-like fashion. Non-woven material may be made from a variety of processes, including but not limited to air-laid processes, melt blown processes, wet-laid processes, hydroentangling processes, staple fiber carding and bonding, spun bond processes and solution spinning.

A substrate coated according to the method of the present invention can be used in personal care items and absorbent structures, such as diapers, to allow rapid penetration of fluid into the absorbent core without depressing the surface tension of the fluid to be absorbed. Depression of surface tension has been shown to reduce wicking distance within absorbent structures.

After the substrate is treated with the carbohydrate-salt mixture, the substrate is rinsed with a solvent such as water to remove excess salt and regenerate the water insoluble carbohydrate as a hydrophilic coating. Suitable solvents desirably have some solubility in water. In addition to rinsing the substrate with water, the substrate may be rinsed with solvents including, but not limited to alcohols such as ethanol, methanol, and iso-propanol, ketones such as acetone and methyl ethyl ketone, esters including ethyl acetate and acetonitrile. However, water is the most effective solvent in breaking the complex between the salt and the carbohydrate. Regeneration of the carbohydrate on a treated substrate may be accomplished through a two step method by first washing the substrate with a solvent, such as ethyl alcohol, which will dissolve the excess salt, leaving a carbohydrate-salt complex. The substrate is then washed with water. Alternatively, the carbohydrate can be regenerated with a single washing with water, which will both remove excess salt and regenerate the carbohydrate molecule. The choice of method can affect the balance of hydrophilic/hydrophobic properties of the resulting product, and can also affect the economies of the process.

The amount of carbohydrate added to a substrate surface depends on the properties desired. For example, an add-on amount of less than 0.5% cellulose has been found to give a discontinuous layer of cellulose. This would be advantageous in, for example, printing applications, wherein it would be desirable to have a wettable surface, but also desirable for the ink to not be able A to wick across the surface and blur the resulting image. An add-on between 0.5–1.5% cellulose has been found to give a continuous, thin layer of cellulose which is uniformly wettable, but which does not impart a "wet" feeling. Such a layer can provide a continuous path for fluid movement across an interface and is useful in such applications as a body-side liner for an absorbent article, such as a diaper, incontinence product, or feminine care product. Heavier applications of cellulose, greater than 1.5%, give a uniformly wettable surface which can retain significant amounts of liquid and may also provide a "wet" feeling. These higher add-on levels could be useful in products such as wipers, where the high strength of a man-made fiber can be enhanced with the good wetablility of cellulose. Such heavier applications of cellulose could also be useful in absorbent products where both significant liquid retention and a "wet" feeling are desired, such as children's training pants.

Temperature control is a significant part of the present invention. Different complexes form at different dissolution temperatures and concentrations to salt. Desirably, the temperature for dissolution, dilution and application of the coating to the substrate is about 65° C. Temperature has also been found to affect the structure of the carbohydrate formed during the regeneration process, and thus affect observable properties of the product treated with the carbohydrate mixture. Specifically, the highest wettability of the carbohydrate is obtained when the regeneration takes place at about 65° C. to about 85° C.

As an illustration of the method of the present invention, cellulose can be dissolved in an aqueous zinc chloride solution. Cellulose is the most abundant polymer on earth, and consists of a straight-chain polymer of anhydrous glucose with beta 1–4 linkages. Natural cellulose can be obtained from. e.g. wood pulp or cotton. Natural cellulose has a degree of polymerization (DP) in excess of 250,000. While natural cellulose can be dissolved in zinc chloride solution, such a mixture is typically extremely viscous, although it is possible to use the mixture with mechanical assistance. For laboratory purposes, it is common to use lower DP cellulose. Lower DP cellulose is commercially available as Fibrocel (Resources Industry, Lafayette, Ind.) and as Avicel microcrystalline cellulose, grade PH-101 (FMC Corporation, Philadelphia, Pa.). Fibrocel has a DP of approximately 300 and Avicel has a DP of approximately 200. Low DP cellulose can also be prepared in the laboratory by acid treatment of native cellulose by means that are well known to those skilled in the art. Cellulose of even lower DP can be made by acid hydrolysis of cellulose recovered from zinc chloride solution.

These extremely low DP materials can be dissolved in aqueous solutions of salts of lesser Hammett acidity than zinc chloride at ambient temperature. Higher molecular weight cellulose sources require higher Hammettt acidity solutions, and desirably, a higher temperature to dissolve. Desirably, a temperature between about 65° C. and about 85° C. is used. At temperatures above 85° C., a rapid reduction in DP occurs. In all cases, dissolution of the carbohydrate causes some reduction in DP. For high DP cellulose, this reduction is desirable to produce a mixture with an appropriate viscosity for processing according to the method of the present invention. A viscosity range of about 1 to about 150 centipoise (cp) is desirable, a range of about 1 to about 100 cp is preferred, and a range of about 1 to about 50 is most preferred. The mixture can be quickly cooled when the viscosity has reached the desirable range. Alternatively, a carbohydrate-salt mixture of native cellulose in zinc chloride can be held at a moderate temperature, such as 50° C., for a lengthy period, such as overnight, in order to reduce the viscosity to a desirable range.

The concentration of aqueous zinc chloride used to dissolve the cellulose can range in concentration from about 55% by weight zinc chloride in water to a saturated solution of zinc chloride in water. Desirably, the concentration of zinc chloride ranges from about 62% to about 76% by weight. Concentrations below about 55% by weight zinc chloride have been found to swell cellulose, but not dissolve it. The concentration of cellulose in the mixture should be from about 0.1% to about 45% by weight. The concentration of cellulose is a significant factor in the viscosity of the final mixture and a preferred range for laboratory experiments would be from about 0.1% to about 5.0% by weight, more desirably from about 1.0% to about 4.0% by weight. The use of mechanical equipment adapted to handling high viscosity mixtures could change the preferred range to higher concentrations of cellulose.

As mentioned above, heating the carbohydrate-salt mixture affects the degree of polymerization of the carbohydrate. In addition, the temperature affects the manner in which the zinc ions coordinate with the glucose residues of the cellulose chain, which in turn affects the hydrophilic properties of the cellulose after regeneration.

After the mixture of cellulose in zinc chloride is formed, it can be diluted with water to control the orientation and degree of aggregation of the cellulose-zinc complex. The degree of dilution can range from zero to the point where the salt solution is no longer able to hold the carbohydrate in solution, in the case of zinc chloride that dilution would be approximately 40% by weight zinc chloride. Depending on the type of substrate to be coated, a surfactant may be added to the cellulose-zinc mixture so that the mixture will readily wet the substrate.

Finally, the cellulose-zinc mixture is applied to a substrate, such as a non-woven material, by any method known to those skilled in the art. The substrate is rinsed with a solvent to remove the excess zinc chloride and regenerate the cellulose molecule.

As a further illustration of the invention, starch, which is a copolymer of amylose and amylopectin, can be dissolved in aqueous calcium chloride solutions ranging in concentration from 30 weight percent to saturated. Calcium chloride is an inorganic salt of lesser Hammett acidity than zinc chloride and is useful when the hydrogen bonding insolubilizing the carbohydrate is not as strong as in native cellulose. The concentration of starch in the mixture is desirably from 0.1% to 50% by weight. More desirably, the concentration of starch in the mixture is from 0.1% to 10% by weight, because of the mixture viscosity. The use of equipment adapted to handling high viscosity mixtures would change this preferred range. The dissolution takes place over a range of temperatures from room temperature (about 20° C.) to about 85° C. The temperature affects the manner in which the calcium ions coordinate with the sugar residues of the starch chain, which in turn affects the balance of hydrophilic/hydrophobic properties upon regeneration.

The mixture thus formed is diluted with water in order to control the orientation of the calcium-starch complex. The degree of dilution is determined by the properties desired in the final product and can range from no dilution down to a concentration of calcium chloride which is barely able to keep the starch in solution, typically about 10% by weight.

The diluted mixture is applied to a substrate by any method known to those skilled in the art. If necessary, the wettability of the treatment mixture can be increased through the use of a surfactant. The substrate is then rinsed with a solvent to remove the excess calcium chloride and regenerate the starch.

As a further illustration of the invention, chitin, which is known for its wound healing properties, can be suspended aqueous in zinc chloride solutions and heated to at least partially dissolve the chitin. Water or other solvent may then be added to the chitin-salt solution. The solution is then filtered as desired to remove any insoluble fraction, and the filtrate is applied to a substrate by any method known to those skilled in the art. The substrate is then rinsed with solvent to remove excess zinc chloride and regenerate the chitin. Chitin coated substrates prepared according to the foregoing method are useful for incorporation into absorbent products where the wound healing properties of chitin are desirable, such as wound dressings and diapers, where the chitin coating may promote healing of wounds and/or diaper rash.

The present invention is also directed to a coated substrate made according to the method of the present invention. The coated substrate may be incorporated into various absorbent structures including but not limited to personal care products designed to be contacted with body fluids such as diaper liners, feminine pads, panty liners, incontinence products, training pants; and in other absorbent structures such as wipes, bibs, wound dressings and the like.

Those skilled in the art will readily understand that the coated substrate of the present invention may be advantageously employed in the preparation of a wide variety of products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Test Methods

Anthrone Carbohydrate Test

This test is used to determine the amount of carbohydrate present in a sample. A carbohydrate coating on a substrate (0.3 g is a typical size) is hydrolyzed by immersing in 10 ml of 72% sulfuric acid for one hour at room temperature with periodic agitation. A 1–12 ml aliquot of the hydrolyzed carbohydrate is added to a 25 ml volumetric flask and diluted with 72% sulfuric acid solution to a total volume of about 12 ml. 12.5 ml of anthrone test solution (see below) is added to the volumetric flask, which is then stoppered and the contents mixed. After mixing, the stopper is loosened and the flask is immediately suspended in a boiling water bath for 15 minutes. After the 15 minutes reaction time, the flask is cooled in a cold water bath. Once cooled to room temperature, the contents of the flask are made up to 25.0 ml with 72% sulfuric acid. The absorbence of the sample at 625 nm is determined in a visible light spectrophotometer. A reagent blank is prepared by following the same procedure, but using uncoated substrate. Absorbence by the blank is subtracted from that of the sample.

The concentration of carbohydrate is determined by comparing the results to a calibration line. The calibration is prepared by dissolving 5 mg of the starting carbohydrate in 100 ml of 72% sulfuric acid at room temperature for one hour with swirling, then pipetting 0, 1, 2, 5 and 10 ml aliquots of the mixture into a 25 ml volumetric flask and following the procedure above to develop a green color.

The anthrone test solution is prepared by weighing 0.10±0.0005 g of anthrone into a small beaker. 100 ml of 72% sulfuric acid is measured into a graduated cylinder and used to quantitatively transfer the anthrone into a 125 ml Erlenmeyer flask containing a stirring bar. Add any remainder of the 100 ml to the flask. Heat the solution in the flask with stirring through a glass fiber filter paper. Allow the solution to sit for at least four hours before use and discard one day after preparation. Typically, this means that the solution is prepared before the end of the day, allowed to sit overnight, used the next day, and any remaining solution discarded at the end of that day. Sufficient solution must be prepared to perform both the analyses and the calibration.

Fluid Run-Off Test

This test is used to determine the ability of a liner material to allow the passage of fluid into an absorbent structure. In this procedure, a fixed volume of water is dispensed onto a liner material while on a 30° incline. Any water which is not transmitted through to the absorbent material underneath the liner, runs off and is collected and measured. The procedure is fully described in U.S. Pat. No. 5,200,130.

Fluid Intake/Flowback Evaluation Test

This test is designed to measure the absorbency/penetration time, flowback amount and amount of liquid retention in the liner of an absorbent article, such as an infant diaper. The absorbency/penetration time (in seconds) is measured by using a stopwatch and visually determining the length of time required to absorb simulated urine voidings. The flowback test measures, in grams, the amount of liquid that emerges from the "baby side" of the diaper after it has absorbed each of three liquid insults and pressure has been applied. The retention test measures, in grams, the amount of liquid that remains held in the liner component of the diaper. The procedure is fully described in U.S. Pat. No. 5,192,606.

For the tests done with the material prepared in accordance with the present invention, the cover stock of a HUGGIES® step 3 male diaper was cut away and replaced with materials produced according to the teachings of this disclosure.

Vertical Wicking Test

This test is used to evaluate the ability of water to travel vertically in a material with a capillary-like structure. The test is sensitive to both the capillarity and the wettability of the structure. The procedure is to suspend a sample vertically above a container of the test fluid, lower the sample into the test fluid until the bottom of the sample contacts the fluid, and note the time required for fluid to reach particular heights within the body of the sample.

EXAMPLES

Example 1

1000 gm of zinc chloride, (anhydrous, AR grade, Mallinckrodt), was dissolved in 514 g of water to form a 66% aqueous zinc chloride solution. The zinc chloride solution was placed in a water bath and maintained at 65° C. throughout the remaining solution preparation. 16 g of Avicel PH 101 microcyrstalline cellulose (FMC Corporation, Philadelphia, Pa.) that had been previously wetted with 25 g of water, was added to the zinc chloride solution. The mixture was allowed to stir for 30 minutes to ensure complete dissolution of the cellulose. The cellulose-zinc chloride mixture was then diluted with a solution of 2 g Standapol ES3 surfactant (Henkel, Hoboken, N.J.) in 436 g of water at a rate of 2 ml/minute. At the end of the dilution, there was a single mixture, being kept at 65° C., of 50% by weight zinc chloride, 0.8% by weight cellulose, and 0.1% by weight Standapol ES3. This mixture was placed in a shallow pan on a hot plate (Corning PC-35 1, Corning Glass Works, Corning, N.Y., set between "2" and "3" on the dial indicator). A length of spunbonded polypropylene fabric with a basis weight of 0.6 oz/sq yd (Kimberly-Clark Corporation, Neenah, Wis.) was drawn through this mixture, then through a laboratory wringer (Atlas Laboratory Wringer, Atlas Electric Devices, Chicago, Ill.) with the arm weighted to 40 lbs to squeeze out excess mixture. The coated fabric from the wringer was deposited in a tub of distilled water at least 10 minutes and then air dried without further washing. The produced fabric was tested for cellulose content (anthrone carbohydrate test) and found to have from 0.5 to 1.0% cellulose add-on. Further samples were tested for runoff and FIFE and found to be equivalent to standard, surfactant treated diaper liner.

Example 2

189 lbs of 69.5 weight percent zinc chloride solution (Zaclon Inc, Cleveland, Ohio) was heated to 125° F. and used to dissolve a mixture of 2.1 lbs of Avicel PH-101 microcrystalline cellulose (FMC Corp, Philadelphia, Pa.) pre-wet with 4.2 lbs of deionized water. The mixture was diluted with 78 lbs of water containing 125 g of Standapol ES3 (Henkel, Hoboken, N.J.) over one hour and maintained at 145° F. The mixture of cellulose was applied to several hydrophobic substrates on a Faustel coaster (Faustel Inc., Germantown, Wis.) set up in a standard dip and squeeze configuration at various speeds, from 30 feet per minute (fpm) to 500 fpm. The substrates included an 0.5 oz/sq yd bouffant cap fabric, an 0.6 oz/sq yd diaper liner fabric, (both obtained from Kimberly-Clark Corp., Neenah, Wis.) and a polyethylene apertured film (DELNET X220, Applied Extrusion Technologies, Middleton, Del.). The substrates were washed in line with a water spray, but this proved to be inadequate since residual zinc chloride was found on the substrates. Pieces of substrate were further washed with water to remove residual zinc chloride and found to be durably wettable to repeated washings, even at intervals of many weeks. Results from anthrone carbohydrate testing are presented in Table 1. The table also includes the percentage of residual zinc determined by atomic absorption analysis (Galbraith Laboratories, TN).

TABLE 1

Cellulose Add-On To Several Substrates

| Substrate | Machine Speed (fpm) | % Carbohydrate | % Residual Zinc |
|---|---|---|---|
| 0.5 oz/sq yd bouffant cap | 30 | 0.24, 0.28 | 0.35 |
| 0.5 oz/sq yd bouffant cap | 60 | 0.15, 0.17 | 0.36 |
| 0.5 oz/sq yd bouffant | 100 | 0.11, 0.14 | 0.13 |

Example 3

The procedure of Example 1 was followed, except the carbohydrate source was starch and the salt was calcium chloride. Both potato and corn starches were used. The starches were dissolved in a 40 wt % calcium chloride solution containing 1% w/w glucopon 225. The mixtures contained from 1% to 5% starch and were applied to several polypropylene non-woven fabrics. The coated fabric was washed with water and dried. Wettability was assessed qualitatively by observing re-wet of the treated fabric.

Example 4

The procedure of Example 1 was followed, except the carbohydrate source was chitin (practical grade, Sigma). 0.5% chitin was suspended in zinc chloride solution (64% w/w). The mixture was heated at 65° C. for one hour, then filtered to separate the insoluble fraction. The filtrate was used to coat an 0.6 oz/sq yd white polypropylene spunbonded fabric (Kimberly-Clark), as described in Example 1. The coated fabric was then washed with water. Wettability was assessed qualitatively by observing re-wet of the treated fabric.

Example 5

0.5 gm of chitin or chitosan (crab shell type, Sigma Chemical, Milwaukee, Wis.) was suspended in zinc chloride solution (80.5 g zinc chloride from Mallinckrodt and 90 ml of water). The slurry was heated at 80° C. for one hour. The chitin was partially dissolved. Water (70 ml) was slowly added to the slurry in the water bath. The solid fraction was removed by vacuum filtration on a milk filter (The Kendall Company, boston, Mass.) using a 5 inch buchner funnel. One ml of Standapol ES-3 (Henkel Corp. Hoboken, N.J.) was added to the mixture. Fabrics that were coated included 0.6 osy spunbond and 1.0 osy meltblown polypropylene obtained from Kimberly-Clark Corporation, Neenah, Wiss. To coat the fabrics, five ml of chitin mixture was poured on a 8 inch×11 inch polypropylene sheet (spunbond or meltblown), and the liquid spread across the fabrics using a metering rod (R.D.S. Wester, N.Y. The coated sample was then washed with water and air-dried. The sample was tested by transferring 2 ml of saline solution with a pipette on dried fabrics. The diameter of the area that was wetted by water was used as indicator as the effect of the coating.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A method of producing a coating, the method comprising:
    forming a carbohydrate-salt mixture by at least partially dissolving a water insoluble carbohydrate in an aqueous salt solution to form a carbohydrate-salt complex;
    adding water to the carbohydrate-salt mixture to form a diluted carbohydrate-salt mixture to control the orientation and degree of aggregation of the carbohydrate-salt complex;
    adding a surfactant to the diluted carbohydrate-salt mixture;
    applying the diluted carbohydrate-salt mixture to a substrate; and
    rinsing the substrate with water to form a regenerated carbohydrate coating.

2. The method of claim 1, wherein the coating is hydrophilic and non-leaching.

3. The method of claim 1, wherein the carbohydrate is cellulose, starch, pectin, alginic acid, chitin or chemical derivatives thereof.

4. The method of claim 3, wherein the carbohydrate is cellulose.

5. The method of claim 3, wherein the carbohydrate-salt mixture comprises from about 0.1% to about 50% by weight carbohydrate.

6. The method of claim 5, wherein the carbohydrate-salt mixture comprises from about 0.1% to about 10% by weight carbohydrate.

7. The method of claim 1, wherein the aqueous salt solution comprises a salt having a Hammett acidity between approximately +2 and approximately −3.

8. The method of claim 7, wherein the aqueous salt solution comprises a salt having a Hammett acidity between approximately 0 and approximately −2.

9. The method of claim 1, wherein the aqueous salt solution comprises zinc thiocyanate, a zinc halide, cadmium thiocyanate, a cadmium halide, titanium thiocyanate, a titanium halide, zirconium thiocyanate, a zirconium halide, lithium thiocyanate, a lithium halide, calcium thiocyanate, a calcium halide, magnesium thiocyanate, a magnesium halide, strontium thiocyanate, a strontium halide, potassium thiocyanate, a potassium halide, guanadinium thiocyanate, N-methyl morpholine oxide, or mixtures thereof.

10. The method of claim 9, wherein the salt solution comprises zinc chloride.

11. The method of claim 9, wherein the aqueous salt solution comprises at least 30% by weight salt.

12. The method of claim 9, wherein the aqueous salt solution comprises from about 60% to about 80% by weight salt.

13. The method of claim 1, further comprising rinsing the substrate with a solvent selected from the group consisting of ethanol, methanol, iso-propanol, acetone, methyl ethyl ketone, ethyl acetate and acetonitrile.

14. The method of claim 1, further comprising heating the carbohydrate-salt mixture to a temperature between approximately 15° C. and 85° C.

15. The method of claim 14, wherein the dissolution and application steps take place at a temperature of about 65° C.

16. The method of claim 15, wherein the rinsing step takes place at a temperature of about 65° C. to about 85° C.

17. The method of claim 1, wherein the substrate is hydrophobic.

18. The method of claim 1, wherein the substrate is a woven or non-woven material comprising polypropylene, polyethylene, polyester or polyamide.

19. The method of claim 1, wherein the carbohydrate-salt mixture is applied to the substrate by dipping, spraying or foam coating the mixture onto the substrate.

20. The method of claim 1, wherein the surfactant is a cationic surfactant, an anionic surfactant or a nonionic surfactant.

21. The method of claim 20, wherein the surfactant is cetyl trimethyl ammonium bromide, sodium lauryl sulfonate, or ethyoxlated hexanol.

22. A method of producing a coating, the method comprising:
    forming a carbohydrate-salt mixture by at least partially dissolving a water insoluble carbohydrate in an aqueous salt solution to form a carbohydrate-salt complex;
    adding water to the carbohydrate-salt mixture to form a diluted carbohydrate-salt mixture to control the orientation and degree of aggregation of the carbohydrate-salt complex;
    applying the diluted carbohydrate-salt mixture to a substrate; and
    rinsing the substrate with water to form a regenerated carbohydrate coating.

23. The method of claim 22, wherein the coating is hydrophilic and non-leaching.

24. The method of claim 22, wherein the carbohydrate is cellulose, chitin, pectin, starch, or chemically modified forms thereof.

25. The method of claim 24, wherein the carbohydrate is cellulose.

26. The method of claim 24, wherein the carbohydrate-salt mixture comprises from about 0.1% to about 50% by weight carbohydrate.

27. The method of claim 26, wherein the carbohydrate-salt mixture comprises from about 0.1% to about 10% by weight carbohydrate.

28. The method of claim 22, wherein the aqueous salt solution comprises a salt having a Hammett acidity between approximately +2 and approximately −3.

29. The method of claim 28, wherein the aqueous salt solution comprises a salt having a Hammett acidity between approximately 0 and approximately −2.

30. The method of claim 22, wherein the aqueous salt solution comprises zinc thiocyanate, a zinc halide, cadmium thiocyanate, a cadmium halide, titanium thiocyanate, a titanium halide, zirconium thiocyanate, a zirconium halide, lithium thiocyanate, a lithium halide, calcium thiocyanate, a calcium halide, magnesium thiocyanate, a magnesium halide, strontium thiocyanate, a strontium halide, potassium thiocyanate, a potassium halide, guanadinium thiocyanate, N-methyl morpholine oxide, or mixtures thereof.

31. The method of claim 30, wherein the salt solution comprises zinc chloride.

32. The method of claim 30, wherein the aqueous salt solution comprises at least 30% by weight salt.

33. The method of claim 30, wherein the aqueous salt solution comprises from about 60% to about 80% by weight salt.

34. The method of claim 22, further comprising rinsing the substrate with a solvent selected from the group consisting of ethanol, methanol, iso-propanol, acetone, methyl ethyl ketone, ethyl acetate and acetonitrile.

35. The method of claim 22, further comprising heating the carbohydrate-salt mixture to a temperature between approximately 15° C. and 85° C.

36. The method of claim 35, wherein the dissolution and application steps take place at a temperature of about 65° C.

37. The method of claim 22, wherein the rinsing step takes place at a temperature of about 65° to about 85° C.

38. The method of claim 22, wherein the substrate is hydrophobic.

39. The method of claim 38, wherein the substrate is a woven or non-woven material comprising polypropylene, polyethylene, polyester or polyamide.

40. The method of claim 22, wherein the carbohydrate-salt mixture is applied to the substrate by dipping, spraying or foam coating the mixture onto the substrate.

41. The method of claim 22, further comprising adding a surfactant to the carbohydrate-salt mixture.

42. The method of claim 41, wherein the surfactant is cetyl trimethyl ammonium bromide, sodium lauryl sulfonate, or ethyoxlated hexanol.

43. A method of producing a coating, the method comprising:

forming a carbohydrate-salt mixture by at least partially dissolving a water insoluble carbohydrate in an aqueous salt solution to form a carbohydrate-salt complex;

adding water to the carbohydrate-salt mixture to form a diluted carbohydrate-salt mixture to control the orientation and degree of aggregation of the carbohydrate-salt complex;

applying the diluted carbohydrate-salt mixture to a substrate; and rinsing the substrate with a solvent to form a regenerated carbohydrate coating;

wherein the carbohydrate is chitin.

44. The method of claim 43, further comprising filtering the chitin salt mixture to separate any insoluble fraction and applying the filtrate to the substrate.

* * * * *